United States Patent
Chiu et al.

(10) Patent No.: US 10,576,261 B2
(45) Date of Patent: Mar. 3, 2020

(54) DEVICE MALE PORT CLEANER

(71) Applicant: SEISA SOPARFI S.A.R.L., Luxembourg (LU)

(72) Inventors: Aaron Chiu, El Paso, TX (US); Enrique Delgado Macias, Ciudad Juarez (MX); Cesar Aguilera, Ciudad Juarez (MX)

(73) Assignee: TURNSTONE TECHNOLOGIES, LLC, Carson City, NV (US)

( * ) Notice: Subject to any disclaimer, the term of this patent is extended or adjusted under 35 U.S.C. 154(b) by 285 days.

(21) Appl. No.: 15/375,164

(22) Filed: Dec. 11, 2016

(65) Prior Publication Data

US 2017/0165467 A1 Jun. 15, 2017

Related U.S. Application Data

(60) Provisional application No. 62/266,540, filed on Dec. 11, 2015.

(51) Int. Cl.
| | |
|---|---|
| *A61B 50/30* | (2016.01) |
| *A61B 90/70* | (2016.01) |
| *A61J 1/00* | (2006.01) |
| *A61L 2/16* | (2006.01) |
| *A61L 2/18* | (2006.01) |
| *A61M 39/16* | (2006.01) |
| *A61M 39/20* | (2006.01) |
| *B08B 1/00* | (2006.01) |

(52) U.S. Cl.
CPC .......... *A61M 39/162* (2013.01); *A61B 90/70* (2016.02); *A61L 2/18* (2013.01); *A61L 2202/17* (2013.01); *A61L 2202/24* (2013.01)

(58) Field of Classification Search
CPC ......... A61B 19/34; A61B 50/30; A61B 90/70; A61B 2050/3008; A61J 1/00; A61L 2/16; A61L 2/18; A61L 2/186; A61L 2/23; A61L 2202/17; A61L 2202/24; A61M 39/16; A61M 39/162; A61M 39/20; A61M 2205/11; B08B 1/00
USPC ... 134/56 R, 116, 147, 166 C, 166 R, 169 C, 134/172, 198, 201; 422/28, 113, 292, 422/294, 300, 302
See application file for complete search history.

(56) References Cited

U.S. PATENT DOCUMENTS

| | | | |
|---|---|---|---|
| 5,554,135 | A | 9/1996 | Menyhay |
| 6,419,825 | B1 | 7/2002 | Hahmann et al. |
| 7,780,794 | B2 | 8/2010 | Rogers et al. |
| 7,985,302 | B2 | 7/2011 | Rogers et al. |
| 8,065,773 | B2 | 11/2011 | Vaillancourt et al. |
| 8,172,825 | B2 | 5/2012 | Solomon et al. |
| 8,206,514 | B2 | 6/2012 | Rogers et al. |
| 8,252,247 | B2 | 8/2012 | Ferlic |
| 8,336,152 | B2 | 12/2012 | Vaillancourt et al. |
| 8,388,894 | B2 | 3/2013 | Colantonio et al. |
| 9,192,443 | B2 | 11/2015 | Tennican |

(Continued)

FOREIGN PATENT DOCUMENTS

CN 103285413 A 9/2013

*Primary Examiner* — Levon J Shahinian
(74) *Attorney, Agent, or Firm* — Carr Law Firm PLLC

(57) ABSTRACT

The present invention includes a device male port cleaner, and method of use, for cleaning a male port connector, particularly a male port connector for a medical device. The device male port cleaner may be connected to the male port connector to clean and/or disinfect the male port connector.

22 Claims, 8 Drawing Sheets

(56) References Cited

U.S. PATENT DOCUMENTS

| | | |
|---|---|---|
| 9,750,929 B2 | 9/2017 | Ma et al. |
| 10,099,048 B2 | 10/2018 | Chiu et al. |
| 10,357,579 B2 | 7/2019 | Chiu et al. |
| 2006/0030827 A1 | 2/2006 | Raulerson et al. |
| 2009/0062766 A1 | 3/2009 | Howlett et al. |
| 2010/0050351 A1* | 3/2010 | Colantonio ............ A61L 2/18 15/104.93 |
| 2011/0030726 A1 | 2/2011 | Vaillancourt et al. |
| 2011/0124967 A1 | 5/2011 | Morgan et al. |
| 2011/0314619 A1 | 12/2011 | Schweikert |
| 2012/0111368 A1 | 5/2012 | Rahimy et al. |
| 2013/0323117 A1 | 12/2013 | Ma et al. |
| 2015/0273199 A1 | 10/2015 | Adams et al. |

* cited by examiner

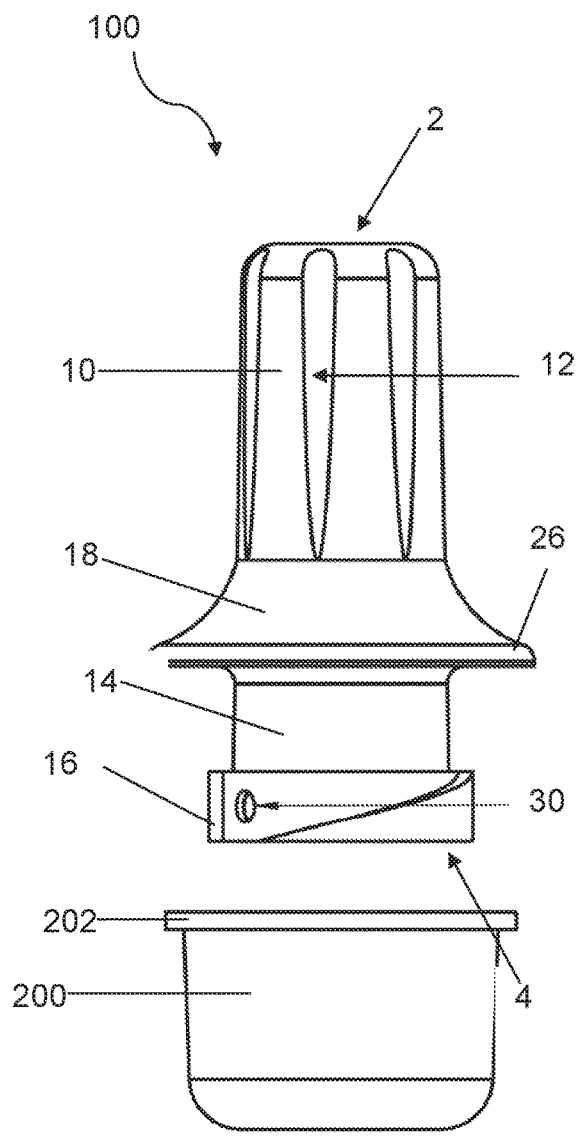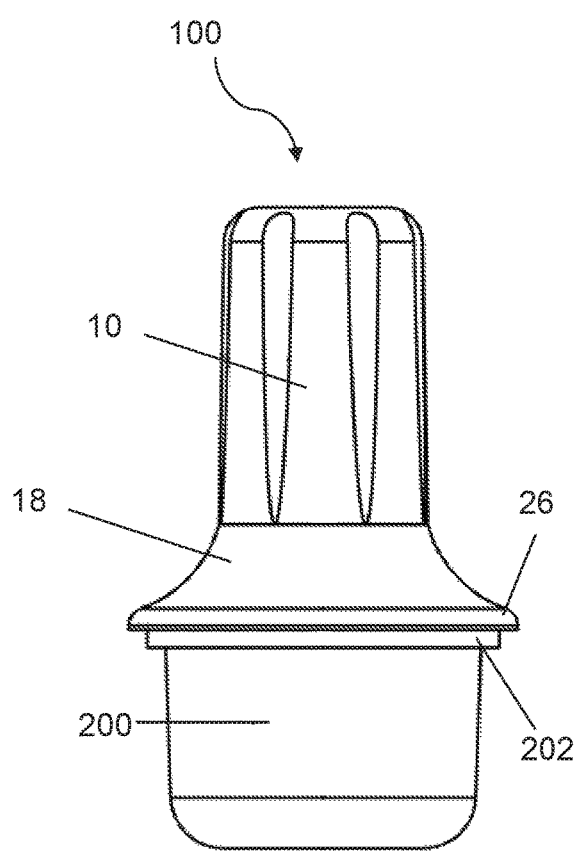
FIG. 1
FIG. 2

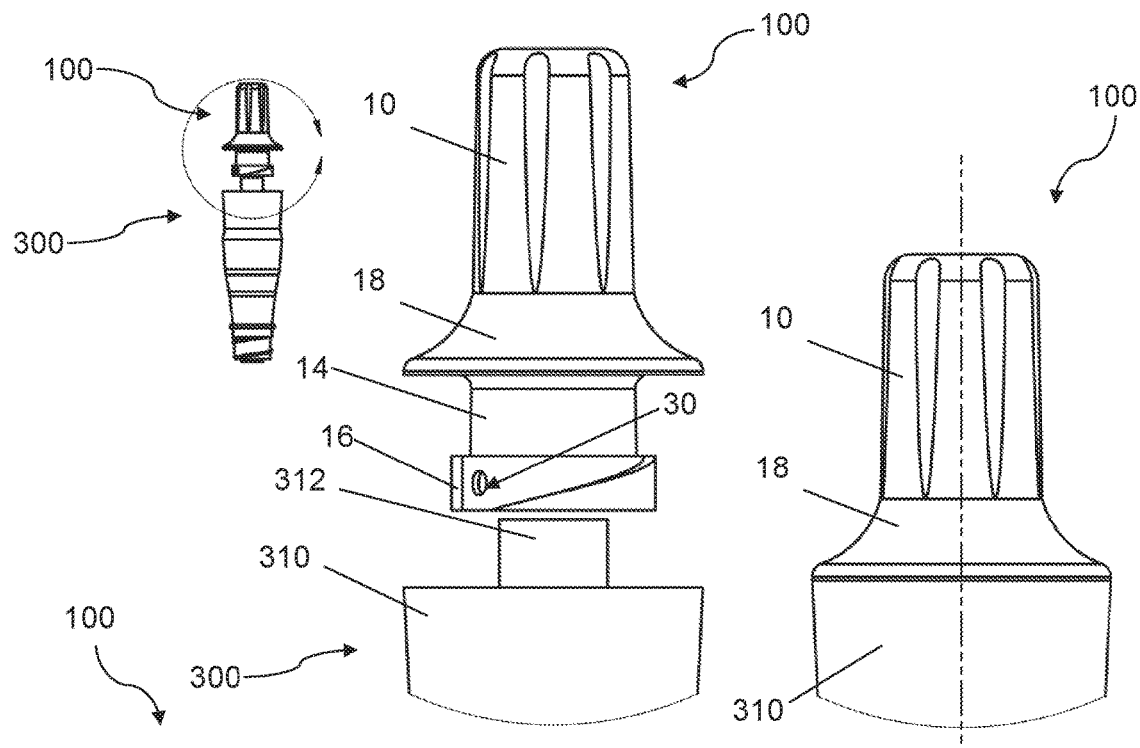
*FIG. 8A*  *FIG. 8B*
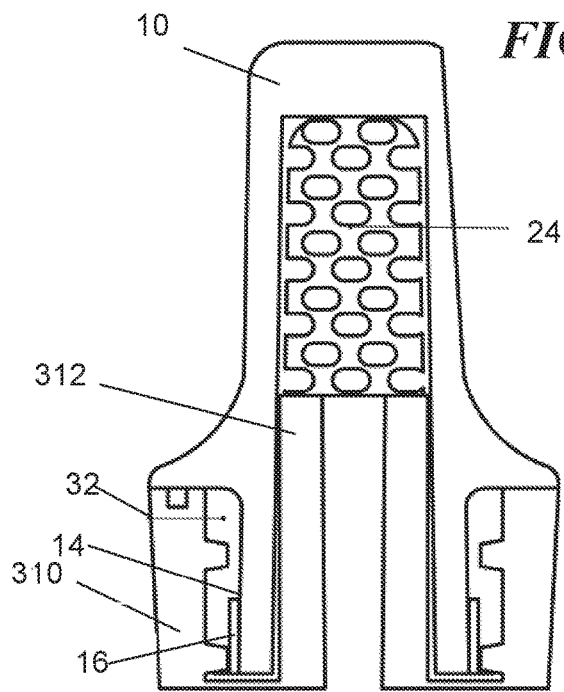
*FIG. 9*

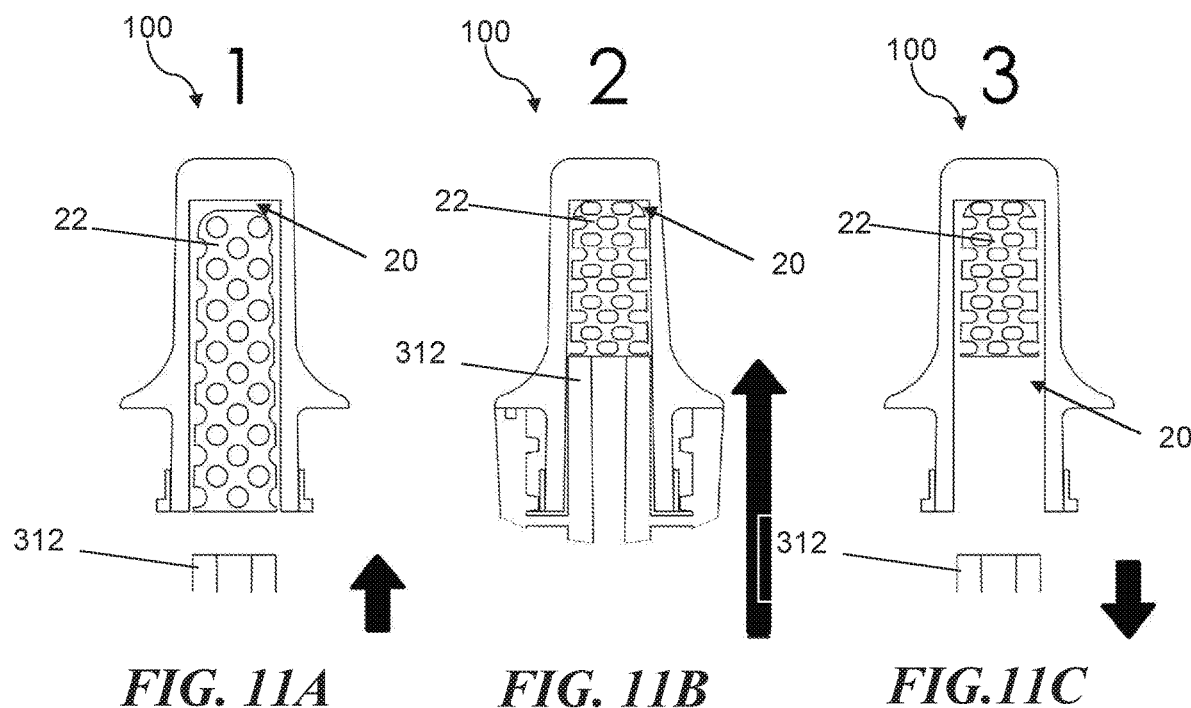
FIG. 11A  FIG. 11B  FIG.11C
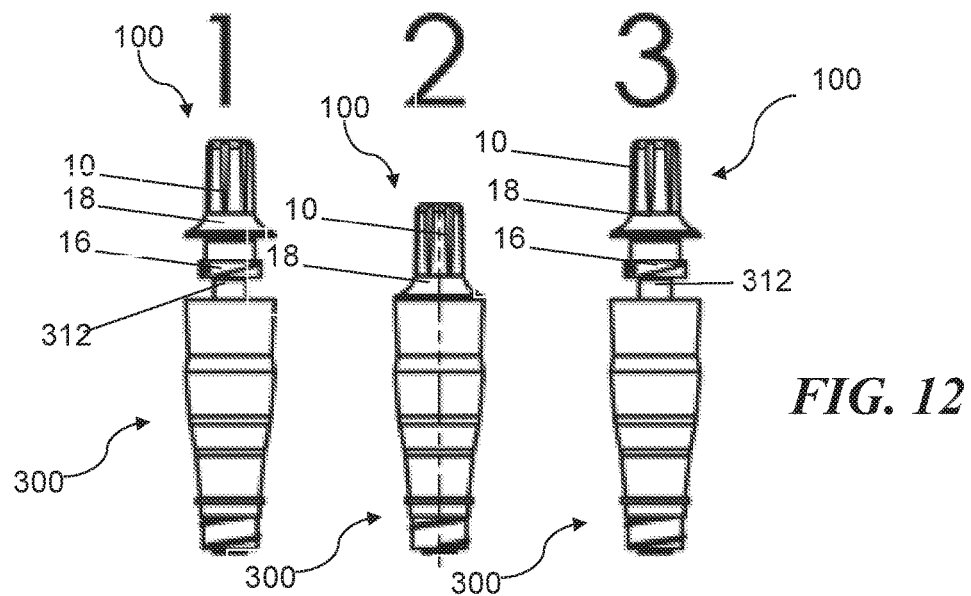
FIG. 12

DEVICE MALE PORT CLEANER

CROSS-REFERENCE TO RELATED APPLICATIONS

This application relates to, and claims the benefit of the filing date of, U.S. provisional patent application Ser. No. 62/266,540 entitled MEDICAL DEVICE MALE PORT CLEANER, filed Dec. 11, 2015, the entire contents of which are incorporated herein by reference for all purposes.

BACKGROUND OF THE INVENTION

Field of the Invention

The present invention relates to device male ports, and more particularly to an apparatus and a method for cleaning and/or decontaminating device male ports, including medical device male ports.

Description of the Related Art

When treating patients in the medical field, there is a need to prevent the transmission of pathogens into or onto a patient from a potentially contaminated surface of a medical implement, or "site" when infusing fluids or aspiration of fluids to or from a patient. Such pathogens include microorganisms such as bacteria and viruses. The transmission of pathogens into a patient may result in an infection that could be life threatening. Contamination by microorganisms may occur via extrinsic or intrinsic contamination. Extrinsic contamination may occur when preparing or administering medications via vascular access systems. Intrinsic contamination may occur during the manufacturing of the device or medication. Extrinsic contamination may be derived from many possible sources including entry points in the administration sets as well as intravenous line connections between different intravenous sets. Other sources for contamination may include during compound medication preparation, improper use of equipment, improper temperature control, improper sterilization/preparation techniques, or methods.

An important aspect in preventing infections as related to connectors includes the constant change of dressings and careful attention to maintaining hygienic and aseptic access to the connector. Traditionally, cleaning a potentially contaminated surface includes a protocol of alcohol swabbing prior to making the necessary connections to the site. However, a poorly swabbed site can carry microorganisms that, if allowed to enter a patient's body, can cause serious harm. Sometimes, much of medical implements used may be so small that it may be difficult to properly cleanse all portions of the implement, particularly the connecting portions of medical device ports. Even more difficult is the ability to clean the interior surface of device ports that are difficult to access. Therefore, it is desired to provide a cleaning device that is simple, economical to manufacture, and effective in cleaning the interior and exterior surface of device ports, particularly medical device male ports.

SUMMARY

Provided is a device male port cleaner, and method of use, for cleaning a device male port that may be inserted into the device male port cleaner.

BRIEF DESCRIPTION OF THE DRAWINGS

For a more complete understanding of the features and advantages thereof, reference is now made to the following Detailed Description taken in conjunction with the accompanying drawings, in which:

FIGS. 1 and 2 show an embodiment of a device male port cleaner and a device cap separated and connected, respectively;

FIGS. 8A and 8B show the device male port cleaner being connected to a male port connector;

FIG. 9 is a cross-sectional view of the device male port cleaner connected to the male port connector;

FIG. 11A-11C is a cross-sectional view of the male port connector being inserted into the device male port cleaner for cleaning before being withdrawn; and FIG. 12 shows an embodiment of a male port connector being inserted into the device male port cleaner for cleaning before being withdrawn.

DETAILED DESCRIPTION OF THE INVENTION

Figure 3:
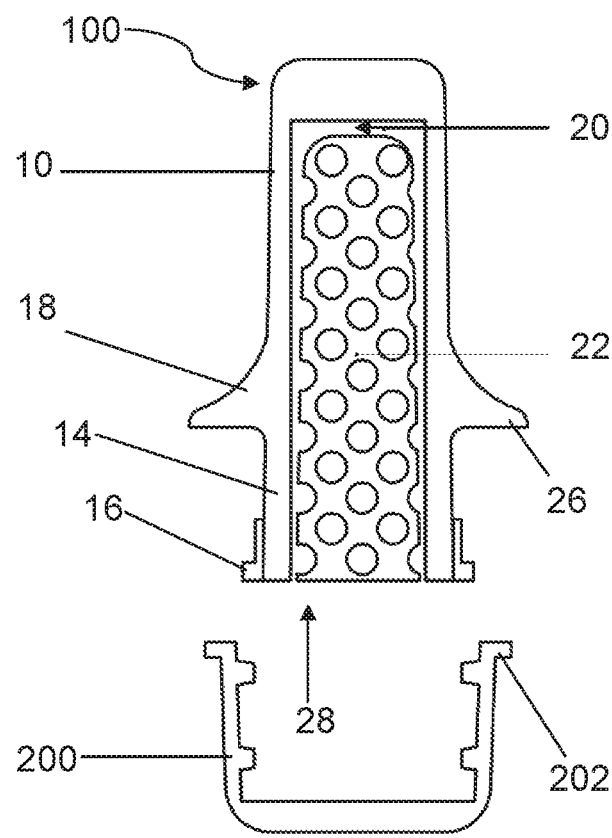
FIGS. 3 and 4 is a cross-sectional view of the device male port cleaner and the device cap separated and connected, respectively.

In the following discussion, numerous specific details are set forth to provide a thorough understanding of the present invention. However, those skilled in the art will appreciate that the present invention may be practiced without such specific details. In other instances, certain specific details, and the like have been omitted inasmuch as such details are not considered necessary to obtain a complete understanding of the present invention, and are considered to be within the understanding of persons of ordinary skill in the relevant art.

In FIGS. 1-12, a device male port cleaner 100 with a device cap 200 is shown. In an embodiment, the device male port cleaner 100 may be coupled to a male port connector to coat the male port connector with an antimicrobial disinfecting solution for disinfection. Prior to being used, the device cap 200 may be secured over the device male port cleaner 100 to seal and protect the connecting end of the device male port cleaner 100 from contamination and other environmental hazards.

Turning to FIGS. 1 and 2, an embodiment of the device male port cleaner 100 and the device cap 200 is shown. According to the embodiment in FIG. 1, the device male port cleaner 100 may comprise a distal end 2 and a proximal end 4. The distal end 2 may further comprise a handle 10 for gripping the cleaner 100 by the user. The handle 10 may further comprise grooves 12 for traction when handling the cleaner 100. The proximal end 4 of the cleaner 100 may comprise the connecting portion of the cleaner 100 with a female luer 14 being used to connect the device male port cleaner 100 to male port connectors needing to be cleaned. The female luer 14 may further comprise a luer lock 16 for securing the cleaner 100 to the outer encasing of male port connector being cleaned. The device male port cleaner 100 may further comprise a flange 18 formed between the handle 10 and the female luer 14. The flange 18 may comprise a circular ring structure formed around the outer circumference of the cleaner 100 and curving outwards away from the outer surface of a transition area between the handle 10 and the female luer 14. The flange 18 may curve outwards as it extends away from the outer surface of the cleaner 100 resembling much of a skirt looped around the cleaner 100. When the female luer 14 is connected to a male port connector for cleaning, the flange 18 may contact an outer casing of the male port connector to form a seal around the female luer 14 and the inner portions of the male port connector. The seal formed by the flange 18 and the outer casing of the male port connector may aid in preventing contamination during the cleaning of the male port connector and maintain its sterility after.

Each of the components making up the device male port cleaner 100 may be made of various semi-rigid to rigid materials, including plastic, aluminum, polymer, stainless steel, silicone based material, synthetic isoprene, isoprene, and thermoplastics. This listing is illustrative, only, and not intended to be exhaustive. It should be appreciated by one skilled in the art that a wide range of materials or mixtures of materials, with properties similar to the above-listed materials may be used to construct the device male port cleaner 100. In alternative embodiments, the device male port cleaner 100 may be provided with additional, fewer, or different components that those of the embodiment shown. For example, in an embodiment, two or more of the components of the cleaner 100 may be combined within a single component, such as the handle 10 and the flange 12, female luer 14 and luer lock 16, or the handle 10 and the female luer 14. Alternatively, for ease of manufacturing, the entire cleaner 100 and all of its components may also be formed as a single unitary structure.

In an embodiment, as shown in FIG. 2, the device cap 200 may be secured to the device male port cleaner 100 to prevent contamination of the connecting portion of the cleaner 100 prior to use. The device cap 200 may be secured over the proximal end 4 of the cleaner 100 to encase the female luer 14 within a sealed environment to maintain its sterility. When the device cap 200 is secured to the cleaner 100, the opening edge 202 of the device cap 200 may be coupled with the outer edge 26 of the flange 18 to create a seal around the proximal end 4 and the female lure 14 of the device male port cleaner 100. The device cap 200 may operate to minimize contamination as well as protect the proximal end 4 of the cleaner 100 prior to use. The outer edge 26 of the flange 18 may be substantially the same shape and size, or slightly larger than the opening edge 292 of the device cap 200 such that when the two surfaces are coupled together, a seal may be created between the flange 18 and the device cap 200. The device cap 200 may be made of various semi-rigid to rigid materials, including plastic, aluminum, polymer, stainless steel, silicone based material, synthetic isoprene, isoprene, and thermoplastics. This listing is illustrative, only, and not intended to be exhaustive. It should be appreciated by one skilled in the art that a wide range of materials or mixtures of materials, with properties similar to the above-listed materials may be used to construct the device cap 200.

Figure 4:
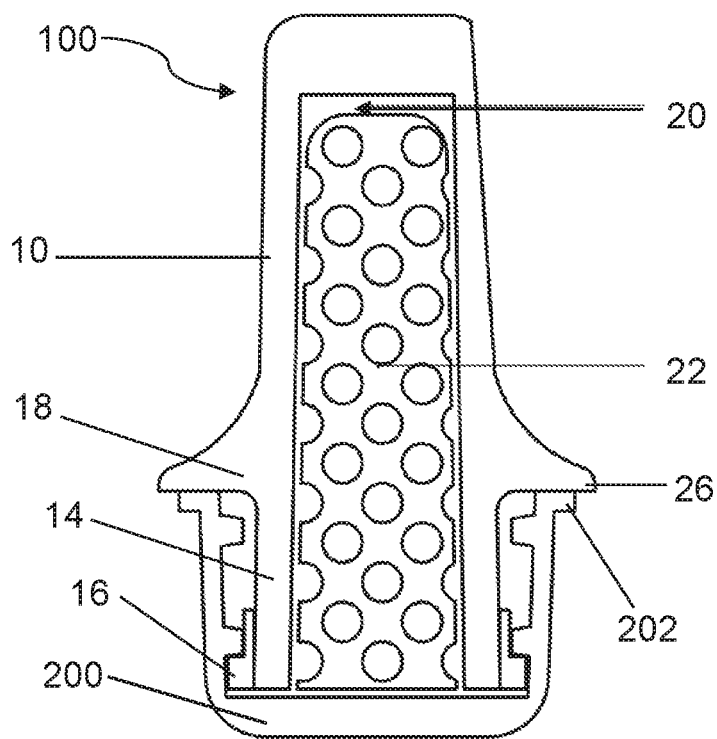

Turning to FIGS. 3 and 4, the device male port cleaner 100 may also comprise a reservoir 20 that starts from an opening 28 in the female luer 14 at the proximal end 4 of the cleaner 100. The reservoir 20 may then extend internally within the cleaner 100 towards the distal end 2 within the handle 10. The shape of the cutout in the device male port cleaner 100 for the reservoir 20 may include but is not limited to a cylinder, a prism, a rectangular prism, a triangular prism, a tube, a pyramid, and the like. The reservoir 20 may further contain at least one of an absorbent material 22 and a disinfecting agent 24. The absorbent material 22 may be soaked in the disinfecting agent 24 prior to use to absorb and hold the disinfecting agent 24 within the reservoir 20.

Figure 5:
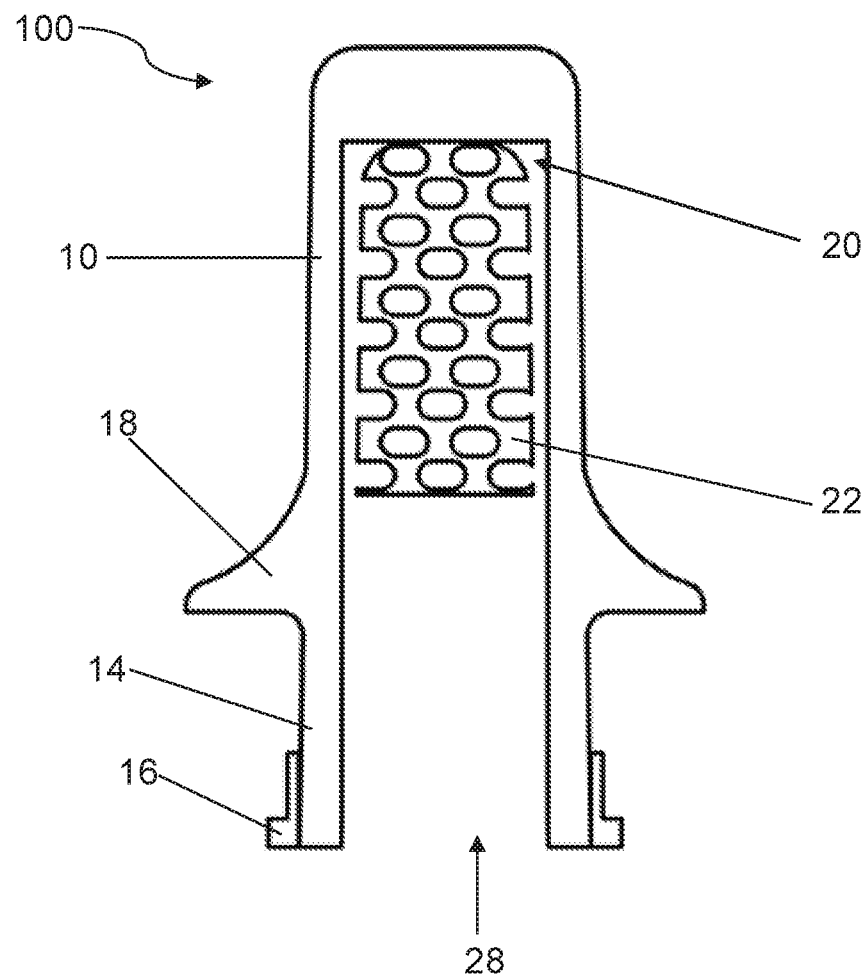
FIG. 5 is a cross-sectional view of the device male port cleaner with an absorbent material compressed.
Figure 10:
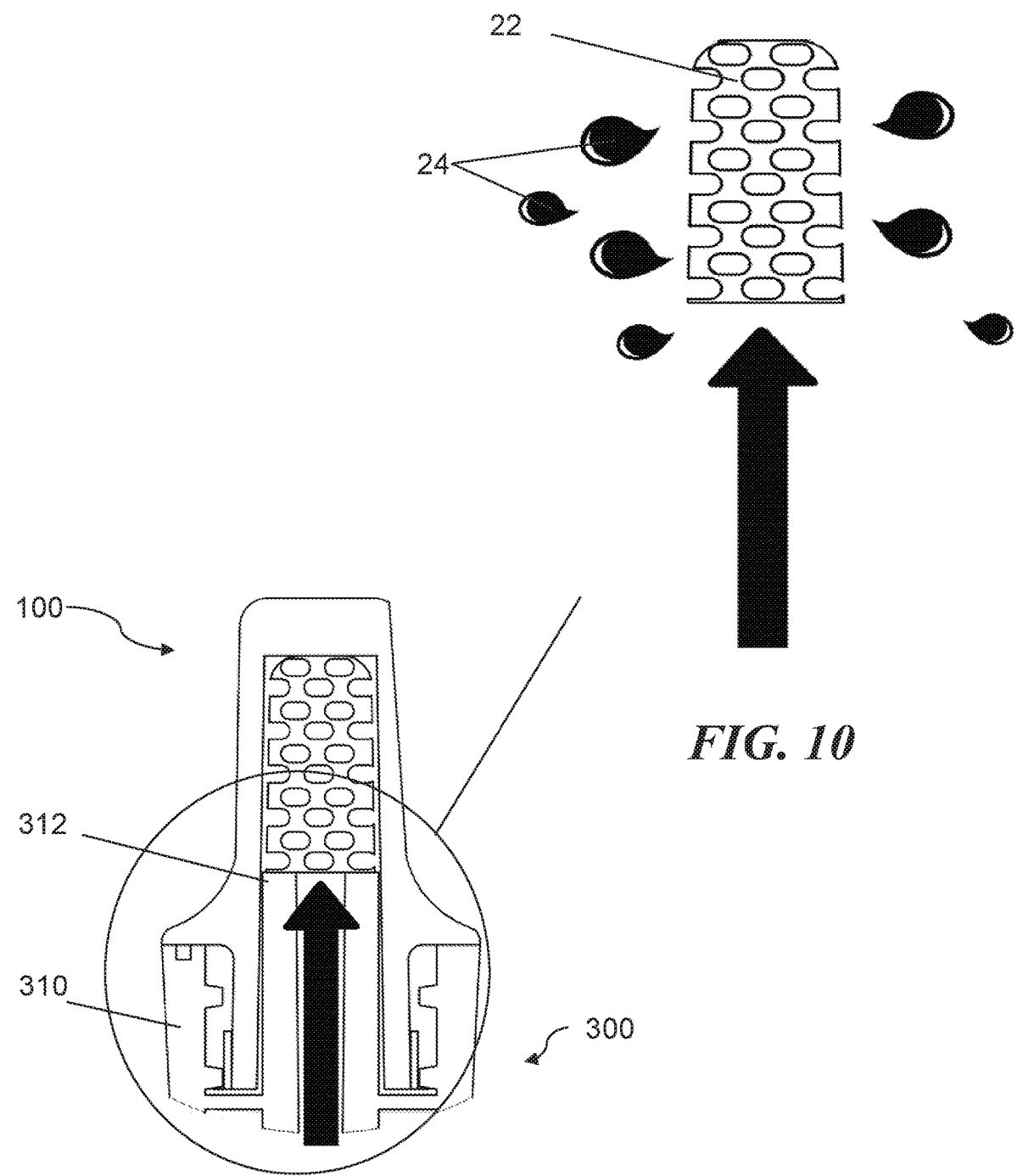
FIG. 10 is a cross-sectional view of the absorbent material releasing a disinfecting agent when the male port connector is inserted into the device male port cleaner.

24. As shown in FIGS. 5 and 10, the absorbent material 22 may be secured within the reservoir 20 such that the absorbent material 22 remains compressible. Compressing the absorbent material 22 may act as a release mechanism for releasing and dispersing the disinfecting agent 24 being held by the absorbent material 22. The absorbent material 22 may be sized and shaped to fit within the reservoir 20 such that the absorbent material 22 may match the corresponding shape of the cutout used for forming the reservoir 20. The absorbent material 22 may be formed from any absorbent, porous, and compressible material including but not limited to a sponge, absorbent cotton, polyurethane, polyvinyl alcohol, silicone, cellulose wood fibers, foam, and foamed plastic polymers. FIG. 4 shows that when the device cap 200 is secured to the device male port cleaner 100, the absorbent material 22 and the disinfecting agent 24 are sealed within the reservoir 20 to be protected from contaminants and environmental hazards. The reservoir 20 may therefore be sized to substantially fit both a male port connector to be inserted into the reservoir 20 and the absorbent material 22 once compressed and the disinfecting agent 24 released.

The reservoir 20 may also contain the disinfecting agent 24 only without the use of the absorbent material 22. The disinfecting agent 24 may be used for cleaning connecting ports inserted into the device male port cleaner 100. In an embodiment, the disinfecting agent 24 may be any antimicrobial or antiseptic agent including but not limited to isopropyl alcohol, povidine iodine, and the like. The disinfecting agent 24 may also be in a liquid, gel, or hydrogel form with various viscosities. The disinfecting agent 24 may be initially contained within the absorbent material 22 before being released or sealed within the reservoir 20 of the device male port cleaner 100 until exposed to a male connecting port inserted into the device male port cleaner 100.

As shown in FIG. 1, the luer lock 16 may further comprise various threading features and designs along the outer surface of the female luer 14 to enable the device male port cleaner 100 to be secured by being threaded into the male port connector intending to be cleaned. The threading features may be formed by curves planes extending diagonally around the circumference and outer surface of the female luer 14. The luer lock 16 may also comprise an opening 30 that extends through the female luer 14 to enable the disinfecting agent 24 when dispersed to also flow out and coat the outer surface of the luer lock 16. With the outer surface of the luer lock 16 also exposed to the disinfecting agent 24, the threading movement to secure the cleaner 100 to the male port connector for cleaning may further disperse and contact the disinfecting agent 24 along the interior surfaces of the connector. The threading of the disinfecting agent 24 coated luer lock 16 within the connector may aid in cleaning the connector's interior threaded surfaces. In addition to the embodiment shown, the threading features along the luer lock 16 may be adjusted to various shapes, sizes, and designs to complement the various male port connectors known to one skilled in the art and that the device male port cleaner 100 may be used with. In an alternative embodiment, the luer lock 16 may not comprise any threading at all. As shown in FIGS. 3 and 4, the device cap 200 may also further comprise threading along the interior surface of the device cap 200 so that the device cap 200 may also be threaded over the luer lock 16 and the female luer 14 when being secured to the cleaner 100. The threading along the interior of the device cap 200 may aid in ensuring that the device male port cleaner 100 is sealed for sterility, and that the device cap 200 is firmly secured to the device male port cleaner 100 and protected prior to use.

Figure 6:
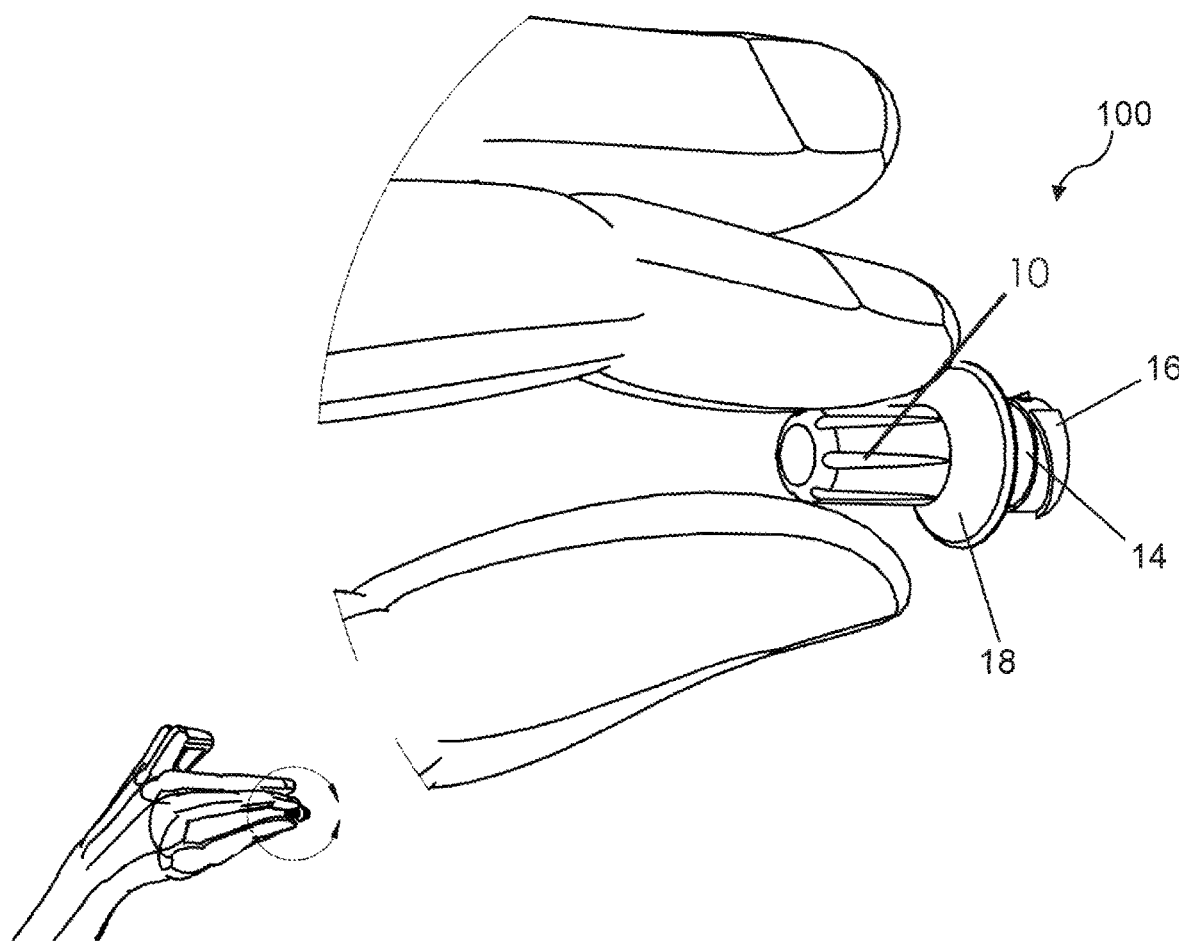
FIG. 6 shows a method of grasping the device male port cleaner.
Figure 7:
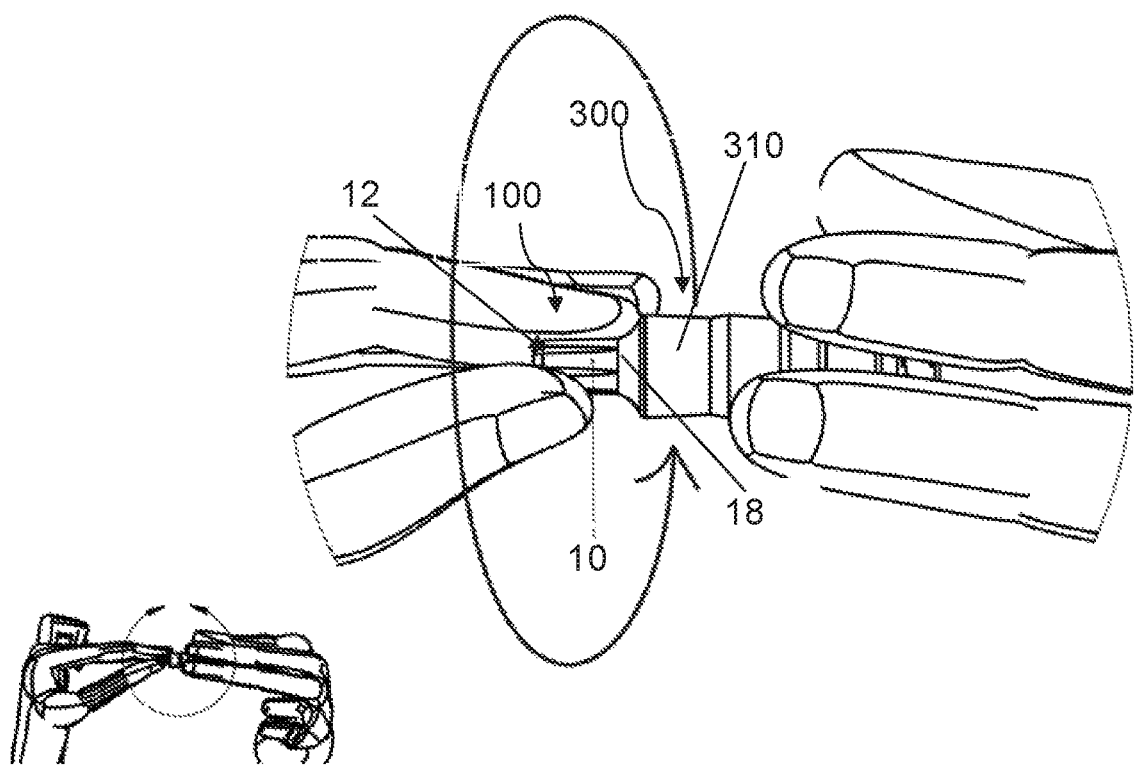
FIG. 7 shows a method of threading the device male port cleaner into a male port connector.

The device male port cleaner 100 may be used to clean various male connecting port connectors related to and including medical device ports such as needle ports, luer locks, catheter hubs, and threaded male connectors used with infusion therapies such as but not limited to intravenous lines, pharmaceuticals, chemotherapeutic drugs, supplements, and intrathecal. Turning to FIGS. 6 and 7, in an embodiment, the device male port cleaner 100 may be connected to a male port connector 300 to disinfect the male port connector 300. The device male port cleaner 100 may be gripped at the handle 10 by a user as shown in FIG. 6 and threaded into the male port connector 300 as shown in FIG. 7. The handle 10 may comprise grooves 12 that aid in creating traction for gripping and the handling the cleaner 100. The grooves 12 may be periodically spaced around the circumference of the outer surface of the handle 10. The grooves 12 may be of various sizes and depth depending on the overall size of the device male port cleaner 100. The handle 10 may comprise various numbers of grooves 12 including 1, 2, 3, 4, etc. The handle 10 may also not have any grooves 12 at all. The device male port cleaner 100 may be secured to the male port connector 300 by threading the luer lock 16 against the interior surfaces of the outer casing 310 of the male port connector 300. The device male port cleaner 100 and the male port connector 300 may be coupled together until the flange 18 of the cleaner 100 contacts the edge of the outer casing 310 of the connector 300. The coupling of the flange 18 and the outer casing 310 may create a seal to maintain the sterility of the male port connector 300 being cleaned by the cleaner 100 prior to use, and to prevent the loss of the disinfecting agent 24 released by the cleaner 100.

Turning to FIGS. 8A and 8B, the device male port cleaner 100 and the male port connector 300 may be operatively connected to disinfect the connector 300 as well as maintain its sterility. An interlocking mechanism between the cleaner 100 and the connector 300 enables a male plug 312 of the connector 300 to be inserted into the cleaner 100 for cleaning as well as create a seal to prevent contamination of the connector 300 after cleaning. When the cleaner 100 is being secured to the connector 300 to disinfect the connector 300, as shown in FIG. 9, the connecting of the cleaner 100 to the connector 300 may comprise an interlocking mechanism such that when the luer lock 16 of the cleaner 100 is threaded into the outer casing 310 of the connector 300, the male plug 312 of the connector 300 may be simultaneously inserted into the female luer 14 of the cleaner 100 and into the reservoir 20. The device male port cleaner 100 may be threaded into the male port connector 300 until the flange 18 contacts the outer casing 310 of the connector 300, as shown in FIG. 8B. The enclosure created by the flange 18 and the outer casing 310 may aid in keeping the male plug 312 sterile prior to being used and minimize contamination. When the male port connector 300 is ready to be used, the cleaner 100 may then be removed to free the male port connector 300 for use.

FIGS. 9 and 10 show that in an embodiment, when the device male port cleaner is threaded into the connector 300, the male plug 312 of the connector is inserted into the reservoir 20 to contact and compress the absorbent material 22. Turning to FIG. 10, when the absorbent material 24 is compressed by the male plug 312 inside the reservoir 20 of the cleaner 100, the compression of the absorbent material 22 acts as a release mechanism for the disinfecting agent 24. Once released from the absorbent material 22, the disinfecting agent 24 may then proceed to clean and disinfect the male plug 312. The compression of the male plug 312 against the absorbent material 22 to release the disinfecting agent 24 occurs simultaneously as the cleaner 100 is being threaded into the connector 300. Once the male plug 312 begins to enter the reservoir 20 as the cleaner 100 is being threaded into the connector 300, the released disinfecting agent 24 inside the reservoir 20 may also flow out of reservoir 20 thorough the opening 30 in the luer lock 16 and be dispersed throughout the interior surface of the outer casing 310. The threading of the luer lock 16 against the interior surface of the outer casing 310 to connect the cleaner 100 may aid in dispersing the disinfecting agent 24 throughout the internally threaded skirt of the outer casing 310. FIG. 9 shows the disinfecting agent 24 flowing through the opening 30 as the cleaner is being threaded may also be dispersed and clean the region 32 of the connector 300. In an alternative embodiment, the reservoir 20 may contain only the disinfecting agent 24 contained by a seal. The disinfecting agent 24 may then be released by the male plug 312 being inserted into the reservoir and breaking the seal.

FIGS. 11A-11C, and FIG. 12 show the device male port cleaner 100 being threaded onto the male port connector 300 to disinfect the connector 300 and then removed to free the connector 300. In FIG. 11A, prior to the cleaner 100 being used to clean the connector 300, the absorbent material 22 within the reservoir 20 of the cleaner 100 is uncompressed and therefore relatively fills the reservoir 20. The absorbent material 22 may be sized so as not to fit the reservoir 20 too tight when uncompressed. This may then leave additional room for the male plug 312 to be relatively easily inserted into the reservoir 20 and the absorbent material 22 compressed, as shown in FIG. 11B, when cleaning the connector 300. After cleaning the male port connector 300 using the device male port cleaner 100, the cleaner may remain secured to the connector 300 prior to the connector 300 being used. This may aid in maintaining the sterility of the connector 300 and minimize contamination after cleaning the connector 300 with the cleaner 100 but prior to use. FIG. 12 shows that the cleaner 100 may be threaded into the male port connector 300 to clean the connector until the flange 18 contacts the outer casing 310 of the connector 300. The flange 18 creates a seal with the outer casing 310 to maintain sterility of the male plug 312 as well as prevent leakage of the disinfecting agent 24.

Having thus described the present invention by reference to certain of its exemplary embodiments, it is noted that the embodiments disclosed are illustrative rather than limiting in nature and that a wide range of variations, modifications, changes, and substitutions are contemplated in the foregoing disclosure and, in some instances, some features of the present invention may be employed without a corresponding use of the other features. Many such variations and modifications may be considered desirable by those skilled in the art based upon a review of the foregoing description of exemplary embodiments. Accordingly, it is appropriate that any claims supported by this description be construed broadly and in a manner consistent with the scope of the invention.

We claim:
1. A port cleaner for cleaning a male port connector, comprising:
  a cleaner body comprising an internal reservoir extending from a proximal end to a distal end wherein the proximal end is configured with an opening for receiv- ing a male port connector, and the internal reservoir comprises an elongated female luer housing;

an absorbent material disposed within the internal reservoir, the absorbent material containing a disinfecting agent;

wherein the proximal end of the cleaner body comprises at least one thread on the exterior surface of the cleaner body; and wherein the reservoir is unobstructed between the absorbent material and the opening of the cleaner body to permit direct contact between the absorbent material and the male port connector inserted through the cleaner body opening and into the internal reservoir and to permit release of the disinfecting agent from the absorbent material directly into the internal reservoir and directly onto the male port connector, in response to the male port connector directly contacting and compressing the absorbent material.

2. The port cleaner in claim 1, wherein the opening in the cleaner body further comprises a cover sealing the internal reservoir of the cleaner body.

3. The port cleaner in claim 2, wherein the cover is bonded over the opening in the port cleaner prior to the port cleaner being used.

4. The port cleaner in claim 1, wherein the absorbent material holds the disinfectant agent prior to being released.

5. The port cleaner in claim 4, wherein compression of the absorbent material inside the cleaner body by inserting the male port connector releases the disinfecting agent within the internal reservoir.

6. The port cleaner in claim 4, wherein the absorbent material comprises a sponge, absorbent cotton, polyurethane, polyvinyl alcohol, silicone, cellulose wood fibers, foam, or foamed plastic polymers.

7. The port cleaner in claim 4, wherein the absorbent material extends inside the reservoir to an entrance into the elongated female luer housing.

8. The port cleaner in claim 1, wherein the at least one thread is configured to secure the port connector to the port cleaner with the male port disposed within the internal reservoir for cleaning.

9. The port cleaner in claim 1, wherein when the port cleaner is threaded with the port connector, the port cleaner is configured to release the disinfecting agent within the internal reservoir to clean the male port connector.

10. The port cleaner in claim 1, wherein the port cleaner comprises a sealing surface external to the internal reservoir configured to couple with a corresponding surface of the male port cleaner, to form a seal preventing release of the disinfecting agent from the internal reservoir.

11. The port cleaner in claim 1, wherein an outer surface of the distal end of the port cleaner is configured as a handle for manipulating the port cleaner.

12. A port cleaner for cleaning a male port connector, comprising:

a cleaner body comprising an internal reservoir extending from a proximal end to a distal end wherein the proximal end is configured with an opening for receiving a port connector;

wherein the opening at the proximal end comprises a luer lock disposed on an exterior surface of the cleaner body;

an absorbent material within the internal reservoir of the cleaner body configured to release a disinfecting agent into the internal reservoir when the port cleaner is used; and wherein the port cleaner is configured such that the absorbent material releases the disinfecting agent into the cleaner body when the male port connector is inserted into the internal reservoir for cleaning;

a flange extending radially outwardly from the exterior of the cleaner body, disposed between the luer lock and the distal end of the cleaner body; and wherein the flange comprises a sealing surface facing the proximal end of the cleaner body and configured to abut a surface of the male port connector to form a seal of the internal reservoir outside of the internal reservoir.

13. The port cleaner in claim 12, wherein the opening further comprises a cover sealing the internal reservoir and disinfecting agent from the external environment prior to use, the cover comprising a cap having one or more internal threads configured to engage the one or more threads along the external surface of the cleaner body and a surface surrounding the cap opening configured to abut the sealing surface of the flange and seal the proximal end of the internal reservoir.

14. The port cleaner in claim 13, wherein the cover is bonded over the opening in the port cleaner prior to the port cleaner being used.

15. The port cleaner in claim 12, wherein compression of the absorbent material inside the reservoir releases the disinfecting agent within the internal reservoir.

16. The port cleaner in claim 12, wherein the absorbent material comprises a sponge, absorbent cotton, polyurethane, polyvinyl alcohol, silicone, cellulose wood fibers, foam, or foamed plastic polymers.

17. The port cleaner in claim 12, wherein when the port connector is inserted into the internal reservoir of the port cleaner, the port connector contacts the absorbent material inside the reservoir.

18. The port cleaner in claim 12, wherein the port connector and the port cleaner may be threaded together when the port connector is inserted into the port cleaner for cleaning.

19. The port cleaner in claim 12, wherein as the port cleaner is threaded with the port connector, the port cleaner releases the disinfecting agent within the internal reservoir to clean the port connector.

20. The port cleaner in claim 12, wherein when the port cleaner is threaded with the port connector, the seal is formed such that the disinfecting agent cleans an interior portion of the port connector.

21. The port cleaner in claim 12, wherein an outer surface of the proximal end of the port cleaner is configured as a handle for manipulating the port cleaner.

22. A port cleaner for cleaning a port connector, comprising:

a cleaner body comprising an internal reservoir extending from a proximal end to a distal end wherein the proximal end is configured with an opening entering into an elongated female luer formed by the internal reservoir and containing an absorbent material, the female luer configured for receiving a male port connector, and wherein the internal reservoir opening is in direct fluid communication with the absorbent material to permit direct contact between the absorbent material and the male port connector when inserted into the internal reservoir;

wherein the cleaner body comprises one or more threads extending along an exterior surface of the cleaner body adjacent to the opening and configured to thread with the male port connector outside of the internal reservoir;

wherein the cleaner body is configured to release a disinfecting agent contained by the absorbent material into the internal reservoir and directly onto the male port connector when the male port connector is inserted into the internal reservoir;

a cover sealing the internal reservoir and disinfecting agent from the external environment prior to use; and wherein the port cleaner is configured such that the absorbent material releases the disinfecting agent into the internal reservoir in response to direct contact compression of the absorbent material by insertion of the male port connector into the internal reservoir.

* * * * *